United States Patent
El-Habnouni et al.

(10) Patent No.: US 11,566,208 B2
(45) Date of Patent: *Jan. 31, 2023

(54) CORE-SHELL MICROCAPSULE WITH A POLYAMINE-BASED THERMOSETTING SHELL

(71) Applicant: GIVAUDAN SA, Vernier (CH)

(72) Inventors: Sarah El-Habnouni, Jurong (SG); Vladica Bocokic, Rueil-Malmaison (FR); Ian Michael Harrison, Poissy (FR)

(73) Assignee: GIVAUDAN SA, Vernier (CH)

( * ) Notice: Subject to any disclaimer, the term of this patent is extended or adjusted under 35 U.S.C. 154(b) by 36 days.

This patent is subject to a terminal disclaimer.

(21) Appl. No.: 16/768,183

(22) PCT Filed: Dec. 18, 2018

(86) PCT No.: PCT/EP2018/085571
§ 371 (c)(1),
(2) Date: May 29, 2020

(87) PCT Pub. No.: WO2019/121738
PCT Pub. Date: Jun. 27, 2019

(65) Prior Publication Data
US 2020/0308513 A1 Oct. 1, 2020

(30) Foreign Application Priority Data
Dec. 21, 2017 (GB) .................................. 1721585.6

(51) Int. Cl.
| | | |
|---|---|---|
| *C11D 3/50* | (2006.01) | |
| *A61K 8/11* | (2006.01) | |
| *A61K 8/81* | (2006.01) | |
| *B01J 13/16* | (2006.01) | |
| *C11D 17/00* | (2006.01) | |

(52) U.S. Cl.
CPC ................ *C11D 3/505* (2013.01); *A61K 8/11* (2013.01); *A61K 8/817* (2013.01); *B01J 13/16* (2013.01); *C11D 17/0039* (2013.01)

(58) Field of Classification Search
CPC ........ A61K 8/11; A61K 2800/10; A61K 8/84; A61K 8/817; A61Q 13/00; A61Q 19/00; B01J 13/14; B01J 13/16; B01J 13/22; C11D 17/0039; C11D 3/505
See application file for complete search history.

(56) References Cited

U.S. PATENT DOCUMENTS

| | | |
|---|---|---|
| 2016/0168510 A1 | 6/2016 | Tasker et al. |
| 2016/0250109 A1 | 9/2016 | Dreher et al. |

FOREIGN PATENT DOCUMENTS

| | | | |
|---|---|---|---|
| EP | 1797947 A2 | 6/2007 | |
| GB | 1598988 A | 9/1981 | |
| WO | 2013068255 A1 | 5/2013 | |
| WO | 2016061439 A1 | 4/2016 | |
| WO | WO-2016061439 A1 * | 4/2016 | ............. A61K 8/042 |
| WO | 2016071152 A1 | 5/2016 | |
| WO | 2016141171 A1 | 9/2016 | |
| WO | 2017001672 A1 | 1/2017 | |
| WO | 2017007552 A1 | 1/2017 | |
| WO | WO-2017007552 A1 * | 1/2017 | ............. B01J 13/185 |

OTHER PUBLICATIONS

International Search Report and Written Opinion of the International Searching Authority for corresponding application PCT/EP2018/085571 dated Mar. 22, 2019.
GB Search Report for corresponding application GB 1721585.6 dated May 16, 2018.
Dong Mei Xu et al, "Synthesis and Characterization of Dendrimers from Ethylene Diamine and Trimethylolpropane Triacrylate", Journal of Macromolecular Science , Part A—Pure and Applied Chemistry., US, (Feb. 16, 2005), vol. 42, No. 2, doi:10.1081/MA-200046980, ISSN 1060-1325, pp. 211-219, XP055568528 2005.
Gustavo González et al, "Environmentally-friendly processing of thermosets by two-stage sequential aza-Michael addition and free-radical polymerization of amine-acrylate mixtures", Polymer Chemistry, GB, (Jan. 1, 2015), vol. 6, No. 39, doi:10.1039/C5PY00906E, ISSN 1759-9954, pp. 6987-6997, XP055568544 2015.

* cited by examiner

*Primary Examiner* — Blessing M Fubara
(74) *Attorney, Agent, or Firm* — Norris McLaughlin PA

(57) ABSTRACT

A core-shell microcapsule comprising a core containing a functional ingredient and a shell surrounding or at least partially surrounding said core, the shell comprising a thermosetting resin formed by the reaction of shell-forming monomers comprising a polyamine and a material comprising a plurality of olefinic double bonds capable of reacting with the polyamine.

12 Claims, 1 Drawing Sheet

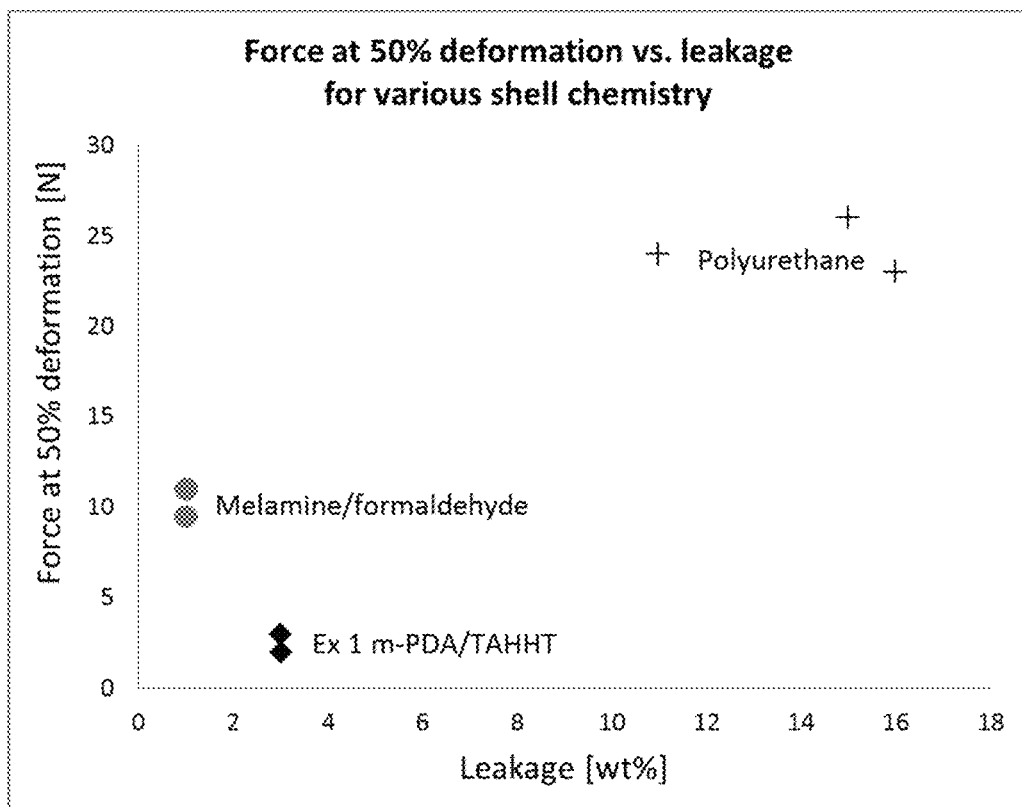

CORE-SHELL MICROCAPSULE WITH A POLYAMINE-BASED THERMOSETTING SHELL

This is an application filed under 35 USC 371 based on PCT/EP2018/085571 filed Dec. 18, 2018, which in turn is based on GB 1721585.6 filed Dec. 21, 2017. The present application claims the full priority benefit of these prior applications and herein incorporates by reference the full disclosures of these prior applications.

FIELD OF THE INVENTION

The present invention is generally concerned with core-shell microcapsules having a shell formed of a polyamine-based thermosetting resin, which is free of any aldehyde or isocyanate residues. The invention is also concerned with encapsulated compositions comprising the core-shell microcapsules, methods of forming same, their use in consumer products, as well as consumer products containing same.

BACKGROUND OF THE INVENTION

Microcapsules have been applied successfully in detergent products for many years, and since their introduction into fabric softener compositions about a decade ago, incorporation of encapsulated perfume compositions in consumer products has experienced year-on-year growth. As the laundry-care industry has come to appreciate the ability of microcapsules to provide an olfactive boost across all stages of fabric treatment or cleaning processes, an expansion of microcapsule use has been observed from fabric softeners and powder detergents, and into liquid detergents and even unit-dose detergent compositions. In personal care, the deodorant category was the first to employ microcapsules, and now microcapsules start to penetrate the personal care industry in shampoos, conditioners and body washes.

This growing industry demand reflects the increasing importance of scent to consumers of personal care, household care and fabric care products. Scent provides an olfactive cue that creates an impression amongst consumers of freshness and cleanliness, which in turn reinforces consumer confidence in the efficacy of such products.

Nevertheless, the demand for microcapsules that are both stable and performant in ever more diverse product types and in ever more challenging (e.g. aggressive or extractive) media creates particular problems for the perfumer.

The commercial success of a consumer product, such as a laundry-care product is dependent in large part upon the manner in which it can evoke a positive response from the consumer. During a cleaning or treatment operation, consumers encounter many touch points with their product. They experience the fresh smell of the product when opening the bottle in which it is contained and when pouring it into a washing machine. They sense the product when removing laundry from a washing machine or from a dryer. They interact with the product when handling fabrics during ironing and folding operations, or when placing or removing fabrics from storage, and of course, when wearing an item of clothing or lying on freshly laundered bed linen. Delivering the right level of fragrance intensity during all of these touch points can create the impression of long-lasting cleanliness and freshness, which can transform a laborious chore into a more pleasant, if not a delightful experience. Furthermore, from a commercial perspective, these moments of pleasure can influence re-purchase decisions of consumers and ultimately create brand loyalty.

The design of microcapsule chemistry, as well as the choice of encapsulated perfume can influence the way in which the microcapsule breaks down during each phase of use of a consumer product. In this way, microcapsules provide the perfumer with the means to control the spatio-temporal release of fragrance across all stages of a cleaning or treatment operation.

A wide variety of encapsulating media has been proposed in the art, including synthetic resins made from polyamides, polyureas, polyurethanes, polyacrylates, melamine-derived resins, or mixtures thereof; or naturally-occurring polymers, such as gelatin, starches, and the like.

As for suitable core materials, in principal, all perfume ingredients on a perfumer's palette can be incorporated to some extent into a core-shell microcapsule. However, it is generally accepted that certain physico-chemical characteristics of a perfume ingredient, for example its calculated log P, will influence whether and to what extent it can be encapsulated, and once encapsulated, its propensity to remain in the core without substantial leakage during storage.

In the hands of the skilled formulator, the judicious selection of both the shell and core materials can result in microencapsulated perfumery that is storage stable in many consumer product bases, and which, in application, is able to modulate the release of fragrance over time, to some extent at least.

Exemplary of the current state of the art core-shell microcapsules are those based on aminoplast resin encapsulating media. Aminoplast core-shell microcapsules comprising an external shell formed of a reaction product of melamine (2, 4, 6-triamino-1,3,5-triazine) and an aldehyde-component, which typically is formaldehyde, although other aldehydes (e.g. glyoxal or glutaraldehyde) have been proposed or employed, are used extensively commercially. State of the art melamine-aldehyde, and particularly melamine-formaldehyde, microcapsules are generally quite resistant to leakage when dispersed in aqueous suspending media, even in surfactant-containing aqueous suspending media, which are regarded as being quite extractive. However, when using these microcapsules the formulator is typically presented with a trade-off between good storage (i.e. leakage) stability and sub-optimal performance in application. More specifically, because melamine-aldehyde capsules can be somewhat resistant to breakage, they tend not to release their core contents under gentle mechanical forces. In the case of laundry applications, the mechanical forces exerted on the microcapsules during the wet stages of application and dry down (i.e. the wash cycle, removing washing from a machine and line drying) are typically not very high and so the fragrance impression consumers perceive can be quite weak, which is problematic because consumers increasingly appreciate the sensation of freshness during these early stages of application.

Another problem with current aminoplast microcapsule technology resides in it being aldehyde-based. Inevitably, aminoplast microcapsules will contain residual amounts of free aldehyde due to unreacted shell-forming monomers, or due to the slow decomposition of aminoplast oligomers over time. Microcapsules, which contain residual aldehyde, or which have the potential for forming aldehyde residues, and particularly formaldehyde residues or glyoxal residues, are less desirable today due to regulatory concerns associated with these aldehyde residues.

Attempts have been made to replace aldehyde-based aminoplast resin encapsulating media by polyurea resin encapsulating media. Although these latter resins have proven to be effective in encapsulating functional ingredients, their preparation requires the use of polyisocyanates, which as with aldehydes, carry their own regulatory issues.

To meet the increasing customer and consumer demands, there is a need within the fast moving consumer goods and perfume industries for new encapsulation chemistries, which can provide microcapsules that possess balanced stability and performance attributes that are at least comparable with, and preferably superior to, existing bench-mark technologies based on melamine-formaldehyde/urea formaldehyde core-shell microcapsules. Furthermore, these chemistries should preferably not produce aldehyde or isocyanate residues.

SUMMARY OF THE INVENTION

In addressing the problems in the prior art, the applicant found in a surprising manner that polyamine monomers could be made to react with acrylic monomers at an oil-water interface, to form an interfacial thermosetting resin. In particular, the applicant found that the reaction can occur in an oil-in-water emulsion medium, in which case the oil droplets become encapsulated by the thermosetting resin. The encapsulating resin obtained in this way is novel and is eminently suitable for use as an encapsulating medium, and more particularly an aldehyde-free encapsulating medium, in the preparation of core-shell microcapsules.

Furthermore, the core-shell microcapsules formed exhibit comparable stability as conventional melamine-aldehyde capsules, but unlike conventional melamine-aldehyde technology, the microcapsules fracture easily such that in application they release fragrance to provide an olfactive signal of freshness during the early stages of a cleaning or treatment process.

Accordingly, in a first aspect the invention provides a core-shell microcapsule comprising a core containing a functional ingredient and a shell surrounding or at least partially surrounding said core, the shell comprising a thermosetting resin formed by the reaction of a polyamine shell-forming monomer and a shell-forming monomer comprising a plurality of olefinic double bonds capable of reacting with the polyamine.

More specifically, amino groups of the shell-forming monomers comprising a polyamine react with double bonds of the material comprising a plurality of olefinic double bonds to form the thermosetting resin.

In a second aspect the invention provides an encapsulated composition comprising a plurality of the core-shell microcapsules referred to above suspended in a suspending medium.

In accordance with a third aspect the invention provides a method of preparing the encapsulated composition, comprising the steps of:
 I) Forming an oil-in-water emulsion, wherein the oil phase comprises a functional ingredient-containing oil droplet dispersed in an aqueous external phase;
 II) Causing shell-forming monomers present in the oil-in-water emulsion to react at the oil-water interface, to form an encapsulating thermosetting resin shell surrounding or at least partially surrounding the oil droplet, thereby forming the microcapsule; and
 III) Optionally, at least partially coating the thermoset resin shell with a functional coating material.

In accordance with a fourth aspect the invention provides a consumer product comprising the encapsulated composition.

In particular embodiments of any of the aspects of the invention, the encapsulated composition is free of any aldehyde residues, particularly formaldehyde residues, as well as any isocyanate residues.

These and other aspects and embodiments of the invention will be further understood in view of the following detailed description of the invention.

DESCRIPTION OF THE DRAWING

FIG. 1 compares the performance (expressed as the elastic force at 50% deformation) and stability (expressed as the percentage of leakage in a model extractive medium), of microcapsules according to the present invention versus conventional melamine-formaldehyde (aminoplast) and polyurea microcapsules.

DETAILED DESCRIPTION OF THE INVENTION

Melamine-formaldehyde core-shell microcapsules have been widely used over many years as delivery vehicles for functional ingredients, such as perfumes or cosmetic actives, in all manner of personal care, household care, and laundry care consumer products. However, even as the demand for encapsulated actives increases, the fast-moving consumer goods industry demands better performing encapsulation technologies, preferably employing encapsulating media that are free of aldehyde (and particularly formaldehyde) or isocyanate residues. This can only be achieved with novel shell chemistry.

A principal issue related to conventional aminoplast resin chemistry is the nature of the so-called pre-condensate that is used as a shell-forming monomer. The pre-condensate is formed by alkylating an aldehyde—most typically formaldehyde. Typically, a polyamine is pre-condensed with the aldehyde to form a polyamine-alkylol pre-condensate, which may then further react to form the resin in a manner known per se. Normally, the alkylol moiety is a methylol or a butylol moiety, with the methylolated form being water-soluble and therefore especially favorable for microencapsulation purposes. It is entirely conventional to employ these alkylolated pre-condensates in the formation of aminoplast resins for use in encapsulation of perfumes and other functional ingredients useful in consumer products. These pre-condensates are popular reagents because, owing to their high solublity in aqueous media, they can be concentrated at the locus of the polyaddition reaction at the oil-water interface, where they can rapidly react to form a resinous shell around the core material and prevent its leakage. However, an issue with their use resides in the fact that they often contain traces of free aldehydes, and in particular free formaldehyde.

In principle, this issue may be solved by replacing the step of alkylating melamine with a polyaddition step in which a polyamine, such as melamine, is reacted with a polyisocyanate to form a polyurea resin. However, as with formaldehyde residues, residues of isocyanates might also give rise to regulatory concerns.

The present invention is based on the surprising discovery that the formation of an alkylolated polyamine or the use of polyisocyanate monomers is not a prerequisite for the formation of polyamine-based resins suitable for encapsulation.

In particular, the applicant has found that it was possible to conduct a poly-addition reaction at an oil/water interface, wherein the poly-addition reaction employs a first shell-forming monomer comprising a plurality of olefinic double bonds, and a second shell-forming monomer, which comprises a plurality of nucleophilic functional groups capable of reacting with the olefinic double bonds on the first shell-forming monomer. Still more particularly, the applicant found that a polyamine, and particularly unprotonated polyamine, such as melamine, reacts spontaneously with the olefinic double bonds on said first shell-forming monomer, such as an ester of (meth)acrylic acid, at the oil/water interface to form the desired resin. This surprising result could not be anticipated from the prior art.

In this surprising manner, it was possible to form microcapsules and encapsulated compositions containing same, which exhibit at least one, and preferably all of the following attributes:

1) The encapsulated compositions of the present invention described herein presented in the form of an aqueous slurry of core-shell microcapsules characteristically possess a high solids content, that is, the compositions contain a level of core-shell capsules on a weight/weight basis relative to the total weight of the slurry that is between 20 and 50%. Still further, the core-shell microcapsules may consist of between about 80 and 95 wt % of encapsulated oil and about 5 and 20 wt % of shell.
2) The encapsulated composition has a functional ingredient loading that is at least 16.5 wt %, and more particular at least about 30 wt %, and still more particularly at least about 40 wt % based on the total weight of slurry (i.e. microcapsule+aqueous phase);
3) The functional ingredients are encapsulated with a very high encapsulation yield, e.g. greater than 90 wt %, and more particularly greater than 95 wt % of the functional ingredient is encapsulated functional ingredient;
4) The microcapsules exhibit a stability-to-release performance balance that is comparable to conventional melamine-formaldehyde capsules; and
5) The microcapsules have an average diameter from about 1 to about 100 micrometers, more particularly from about 2 to about 50 micrometers and still more particularly from about 5 to about 30 micrometers.

The leakage stability of core-shell microcapsules can be assessed according to techniques well known in the art. A convenient method to assess the stability of microcapsules with respect to leakage in extractive media is described in the Examples, herein below.

Microcapsule size is determined in a manner known in the art. A particular method of measuring particle size is light scattering. Light scattering measurements can be made using a Malvern Mastersizer 2000S instrument and the Mie scattering theory. The principle of the Mie theory and how light scattering can be used to measure droplet size can be found, for example H. C. van de Hulst, Light scattering by small particles. Dover, N.Y., 1981. The primary information provided by static light scattering is the angular dependence of the light scattering intensity, which in turn is linked to the size and shape of the droplets However, in a standard operation method, the size of a sphere having a size equivalent to the size of the diffracting object, whatever the shape of this object, is calculated by the Malvern proprietary software provided with the apparatus. In case of polydisperse samples, the angular dependence of the overall scattering intensity contains information about the size distribution in the sample. The output is a histogram representing the total volume of droplets belonging to a given size class as a function of the capsule size, whereas an arbitrary number of 50 size classes can be chosen. Thus, the size obtained is referred to as volume-average particle size.

Experimentally, a few drops of slurry (i.e. the microcapsules in the suspending medium) are added to a circulating stream of degassed water flowing through a scattering cell. The angular distribution of the scattering intensity is measured and analysed by Malvern proprietary software to provide the average size and size-distribution of the droplets (microcapsules) present in the sample. In the case of an unimodal (monodisperse) droplet distribution the percentiles $Dv(10)$, $Dv(50)$ and $Dv(90)$ are used as characteristics of the droplets size distribution, whereas $Dv(50)$ corresponds to the median of the distribution and is taken as a measure of the volume-average size of the microcapsules.

The invention further relates to methods of forming the microcapsules and the encapsulated compositions containing same, as well as the microcapsules and encapsulated compositions made according to said methods, which will be further described herein below.

The method of forming the microcapsules and the encapsulated composition proceeds via the formation of an oil-in-water emulsion. The oil-in-water emulsion may be stabilized using a polymeric stabilizer.

The polymeric stabilizers that are suitable for the purpose of the present invention include water soluble polymers of natural origin, such as cellulose derivatives, degraded or modified starch, gums, pectin, gelatin, and the like; water-soluble polymers of synthetic origin, such poly(vinyl alcohol), poly(vinyl pyrrolidone), poly(acrylic-co-acrylate) copolymers, poly(acrylamide), sulfonated poly(acrylate), copolymers of maleic anhydride with styrene, isobutylene, butadiene and ethylene, poly(styrene sulfonic acid), and the like, and mixtures thereof.

Polymeric stabilizers that are particularly suitable for the purpose of the present invention include copolymers, which are the reaction product of maleic anhydride and an olefinic monomer, such as ethylene, iso-butylene or styrene. Examples of such copolymers include poly (ethylene-co-maleic anhydride), poly (isobutylene-co-maleic anhydride) and poly (styrene-co-maleic anhydride). A particularly preferred copolymer is poly (ethylene-co-maleic anhydride), a commercial grade of which is available under the trade name Zemac e400. The maleic anhydride copolymer may be used singularly or alternatively combinations of maleic anhydride copolymers may be employed.

The maleic anhydride copolymer may be presented for use in the present invention in hydrolyzed form, whereupon the anhydride may be in the form of its free-acid, or its salt, or a mixture thereof.

If a maleic anhydride copolymer is used, it is particularly preferred if it is pre-hydrolyzed before being employed in the emulsification process. Hydrolysis can be achieved by dissolving the maleic anhydride in an aqueous medium, optionally at an elevated temperature, e.g. about 85 to 90° C., for an appropriate time interval. Typically 2 hours is an appropriate time interval to affect hydrolysis. Once the polymer is dissolved under these conditions, the pH of the solution is typically below 3, which is indicative that hydrolysis has taken place. Furthermore, infrared spectroscopic analysis can reveal that the typical absorption bands corresponding to the anhydride group have vanished.

As stated hereinabove, the maleic anhydride copolymer in hydrolyzed form may be presented as its free acid, or its salt form, or a mixture of free acid and salt. The relative amounts of free acid and salt form will depend upon the pH of the aqueous medium. More particularly, the maleic anhydride copolymer is employed in aqueous solution at a pH of from about 2 to about 7, more particularly from about 4 to about 5, where the maleic anhydride copolymer exhibits optimal emulsifier properties.

The maleic anhydride copolymer in hydrolyzed form may be presented as a mixture of its free acid and salt form with monovalent counter-ions, such as lithium, sodium, potassium or ammonium counter-ions.

The maleic anhydride copolymer may be used alone or, preferably, in combination with another polymeric stabilizer, for example a poly(vinyl alcohol).

Poly(vinyl alcohols) that are particularly suitable for the purpose of the present invention are obtained by hydrolysis of poly(vinyl acetate) and have a degree of hydrolysis between 60 and 99%, more particularly between 70 and 98% and still more particularly between 80 and 96%, for example 88±5%. Particularly useful grades form 4 wt % aqueous solutions having a dynamic viscosity at 20° C. of from about 3 to about 50 mPas, more particularly from about 10 to about 30 mPas and still more particularly from about 15 to about 25 mPas, as measured according to DIN 53015 by using the falling/rolling ball viscometer by Höppler having a thermostated falling tube with a diameter of 15.94 mm±0.01 mm positioned at an angle of 80° relative to horizontal and falling/rolling borosilicate with a density of 2.4 g/cm3 and a diameter of 15.81±0.01 mm±0.01 mm for the viscosity range between 0.5 to 10 mPas and 15.6 mm±0.05 mm for the viscosity range between 9 to 140 mPas. For a detailed description of procedure, see for example BROOKFIELD KF10 and KF20, Falling Ball Viscometer Operating Instructions, Manual No. M09-352-C0512, edited by BROOKFIELD ENGINEERING LABORATORIES, Middleboro, Mass. 02346 USA, which is hereby incorporated by reference.

In one embodiment, the poly(vinyl alcohol) hydroxyl equivalent to maleic anhydride copolymer carboxyl equivalent is from about 0.5 to about 20, more particularly from about 1 to about 15, and still more particularly from about 1.5 to about 12.

In a preferred embodiment, the maleic anhydride copolymer is a commercial form of the copolymer available under the trade name ZeMac e400 and the poly(vinyl alcohol) has a hydrolysis grade of 88±5% and a viscosity of from about 20 to about 25 mPas at 20° C., according to DIN 53015, such as Kuraray Poval 23/88, Denka Poval B 17 and the like.

In a preferred embodiment, the level of ZeMac e400 in the emulsion is from about 2 to about 12 wt %, more particularly from about 3 to about 10 wt %, more particularly from about 4 to about 6 wt % and the Kuraray Poval 23/88 to ZeMac e400 weight ratio is from about 0.25 to about 5, more particularly from about 0.5 to about 3 and still more particularly from about 1 to about 2.5.

In another preferred embodiment, the polymeric stabilizer is a polymeric stabilizer formed by the reaction of the polymeric surfactant, such as the maleic anhydride copolymer referred to herein above and a silane that contains a functional group capable of covalently bonding to the shell of a core-shell microcapsule. The silane employed in the preparation of the polymeric stabilizer may be selected from a compound of the Formula I

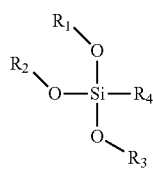

in which $R_1$, $R_2$ and $R_3$ are independently $C_1$-$C_4$ linear or branched alkyl or alkene and $R_4$ is a $C_1$-$C_4$ linear or branched alkyl or alkene comprising a functional group.

Particularly preferred are aminosilanes, and most preferably 3-aminopropyltriethoxy silane.

The aminosilane and the maleic anhydride copolymer, which react to form a polymeric stabilizer may be combined in widely varying amounts. However, it is preferred if the weight ratio of the maleic anhydride copolymer to the aminosilane is within the interval of from about 1/0.05 to about 1/1, more particularly from about 1/0.1 to about 1/0.7, still more particularly from about 1/0.3 to about 1/0.4, for example 1/0.33.

Due to the available alkoxy functional groups on the aminosilane, the polymeric stabilizer does not only act as an emulsifying agent in the preparation of stable emulsions, it can also act as a covalent linker to help bind the shells of to the dispersed oil droplets, resulting in better quality core-shell microcapsules.

The functionalization of the polymeric stabilizer, such that it can covalently link to the shell, through poly-condensation of the alkoxysilane moieties is a particular feature of the present invention.

In the formation of the oil-in-water emulsion, the maleic anhydride copolymer may be added to the aqueous external phase, and the aminosilane may be admixed with the oil phase. Their separation is a process optimization consideration to control the rate of hydrolysis of the silane and to ensure that the silane and the maleic anhydride copolymer react at the oil-water interface in an optimal fashion to form the polymeric stabilizer in-situ. If the aminosilane is allowed to hydrolyze too rapidly it is prone to self-condense. Employing the aminosilane in the oil phase promotes its reaction with the polymeric surfactant at the oil-water interface, rather than undergoing self-condensation. In order to provide optimal reaction conditions for the coupling of the aminosilane and the maleic anhydride copolymer, the pH of the mixture is raised to about 3.5 to 7, for example 4.5 or 6. This can be achieved by the addition of a suitable base. For this purpose, a dilute solution (for example 10% or 20%) of ammonia is suitable, although other bases could be employed, such as dilute sodium hydroxide. The whole process can be carried out over a period of about 1 hour to 3 hours, more particularly 2 hours±0.5 hours, and at ambient, or slightly elevated temperature, e.g. 35±5° C. The polymeric stabilizer formed in-situ in this way becomes associated at the oil-water interface to form an at least partial layer around the oil droplets, stabilizing them and preventing coalescence.

In accordance with the method of the present invention, microcapsules are formed when resinous shells are formed around the emulsion droplets.

Polyamines useful as shell-forming monomers in the preparation of the microcapsules and encapsulated compositions are any suitable shell-forming monomers bearing at least two amino groups, and may be selected from linear or branched aliphatic amines or aromatic amines, or amino-functionalized aliphatic or aromatic heterocycles. Still more particularly, the polyamine is ethylene diamine, bis(2-aminoethyl)amine (CAS #111-40-0), a di- or tri-amino-substituted heterocycle selected from melamine (2,4,6-triamino-1,3,5-triazine), 3,5-diamino-1,2,4-triazole, 2,4-diamino-6-phenyl-1,3,5-triazine, 6-methyl-1,3,5-triazine-2,4-diamine, 1,2-phenylendiamine, 1,3-phenylenediamine or 1,4-phenylenediamine, or mixtures thereof.

Polyamines useful in the present invention do not include polyamine-alkylol precondensates, such as methylolated melamine, which are typically employed in the formation of prior art melamine formaldehyde microcapsules and which are implicated in unwanted aldehyde residue formation.

Polyimines react also with the olefinic double bonds of the first shell-forming monomer, and are therefore also useful for the preparation of microcapsules of the present invention.

The shell-forming monomer comprising the plurality of olefinic double bonds may be any Michael acceptor that is capable of reacting with the afore-mentioned polyamine. The Michael acceptor may contain an olefinic double bond in conjugation with any suitable electron-withdrawing group, such as nitrile, keto, amido, or ester groups. The shell-forming monomer may be a monomer, oligomer or a polymer. Particularly preferred shell-forming monomers are poly-functional amides or (meth)acrylates, although poly-functional acrylates are preferred. Suitable poly-functional acrylates are at least di-functional acrylates, for example tri- and tetra-acrlyates and include, but are not limited to $C_1$-$C_{24}$-alkyl ester(s) of acrylic acid and/or methacrylic acid.

In particular embodiments, the shell-forming monomers may be selected from pentaerythritol-tetraacrylate (PETA), pentaerythritol triacrylate (PETIA), 1,4-butanediol diacrylate (BDA-2), ethylene glycol dimethacrylate (EDGMA), trimethylolpropane triacrylate (TMPTA), hexane diol diacrylate(HDDA), ((2,4,6-trioxocyclohexane-1,3,5-triyl)tris (oxy))tris(ethane-2,1-diyl) triacrylate (TOCTA), Tris(2-acryloyloxyethyl) Isocyanurate, 1,3,5-triacryloylhexahydro-1,3,5-triazine (TAHHT), or mixtures thereof.

In accordance with preferred embodiments of the invention, the shell-forming monomers are those polyamines described above, and in particular melamine; and the Michael acceptor as described above, is more particularly a poly-functional acrylate. Both the polyamine and the poly-functional acrylate must be at least di-functional, that is, they must contain at least two reactive amino-groups or at least two reactive acrylate groups respectively. Furthermore, at least one of either the polyfunctional amine, or poly-functional acrylate must be at least tri-functional to form a cross-linked network.

In preferred embodiments of the present invention, the shell-forming monomers are selected from a polyamine, such as melamine, 1,2-phenylenediamine, 1,3-phenylene diamine and 1,4-phenylediamine, or mixtures thereof, and a poly-functional acrylate, such as Tris(2-acryloyloxyethyl) Isocyanurate and 1,3,5-triacryloylhexahydro-1,3,5-triazine. Without wishing to be bound by any particular theory, it is believed that combinations of any of these particular polyamines and these particular poly-functional acrylates are particularly advantageous, because they may form a flat, and essentially two-dimensional resin structure.

In accordance with the process of the present invention, if desired, a functional coating can be applied to the shells of the core-shell microcapsules. A functional coating may entirely or only partially coat a microcapsule shell. Whether the functional coating is neutral, charged or uncharged, its primary purpose is to alter the surface properties of the microcapsule to achieve a desirable effect, such as to enhance the deposition of the microcapsule on a treated surface, such as a fabric, human skin, hair, or the like. Functional coatings may be post-coated to an already formed microcapsule, or they may be physically incorporated into the microcapsule shell during the shell formation. They may be attached to the shell by physical forces, physical interactions, such as hydrogen bonding, ionic interactions, hydrophobic interactions, electron transfer interactions, or they may be covalently bonded to the shell.

If the functional coating should be attached to the shell by physical association, the chemical structure of the coating will to some extent be determined by its compatibility with the shell chemistry, since there should be some association with the microcapsule shell.

If the functional coating should be covalently bound to the shell, this may be achieved by incorporating into the shell, materials bearing functional groups that are able to react with the coating material.

For example, if the shell of a core shell microcapsule is prepared, as described herein, using a di, tri-, or tetra-functional (meth)acrylate shell-forming monomer, then any residual acrylate functionality present in the shell associated with acrylate shell-forming monomer that does not react with the polyamine during shell formation, can react with coating material to covalently bind the latter to the shell.

Suitable coating materials may be based on polysaccharides, polypeptides, polycarbonates, polyesters, polyolefinic (vinyl, acrylic, acrylamide, polydiene), polyester, polyether, polyurethane, poly-oxazoline, poly-amine, silicone, poly-phosphazine, poly-aromatic, poly-heterocyclic and the like. A more detailed list of coating materials that can be used to coat the microcapsules can be found in the patent literature, for example EP 1,797,947, which discloses coating materials that can be employed as deposition aids, are herein incorporated by reference.

Particularly preferred coating materials may be selected from the group consisting of polymethyl methacrylate, polydimethylaminoethylmethacrylate, polybutyl methacrylate, polydiallydimethylammonium chloride, and mixtures thereof.

If the coating material is a polymer, it can be generated in-situ during the coating process by the polymerization of coating material monomers that contain olefinic double bonds. More particularly, suitable monomers can be added to a slurry of core-shell microcapsules formed according to a process described herein and caused to polymerize as well as react with the aforementioned residual acrylate functional groups in the shell, in order to build-up polymeric coating material that is covalently bound to the shell, and which at least partially coats it.

Suitable monomers for this purpose include but are not limited to acrylates, such as methyl methacrylate, butyl methacrylate, methacrylic acid, dimethylaminoethyl methymethacrylate (DMAEMA), and diallydimethylammonium chloride (DADMAC).

A particular method of preparing microcapsules and an encapsulated composition containing same, comprises the steps of:

I) Forming an oil-in-water emulsion, wherein the oil phase comprises functional ingredient-containing oil droplets dispersed in an aqueous external phase;

II) Causing shell-forming monomers present in the oil-in-water emulsion to react at the oil-water interface, to form a thermosetting resin shells surrounding, or at least partially surrounding, the oil droplets, thereby forming core-shell microcapsules; and III) Optionally, at least partially coating the thermosetting resin shells with a coating material.

As stated herein above, the oil-in-water emulsion can be prepared in the presence of a polymeric stabilizer, wherein preferred polymeric stabilizers are provided by i) a mixture of a maleic anhydride copolymer and poly(vinyl alcohol), or ii) the reaction product of a maleic anhydride copolymer with an aminosilane, as described hereinabove.

Once formed, the oil-in-water emulsion comprising a polymeric stabilizer may be maintained under stirring and at elevated temperature, e.g. about 30° C. or above, more particularly 35° C.±5° C., for a period of time, which may be up to about 2 hours. Such conditions, in particular favour the complexation of the maleic anhydride copolymer and poly(vinylalcohol) or the reaction between the maleic anhydride copolymer and the aminosilane, depending on which polymer stabilizer is selected.

Each of the shell-forming monomers may be added before, during or after formation of the oil-in-water emulsion. Furthermore, the shell-forming monomers may be added simultaneously, separately, or sequentially to the reaction mixture.

With regard to the sequence of addition of the shell-forming monomers, the shell-forming monomer containing a plurality of olefinic bonds may be added to the emulsion before, during or after formation of the oil-in-water emulsion, although it is preferred if it is added after its formation. Furthermore, it is preferred if this monomer is added after addition of the polyamine shell-forming monomer.

The polyamine may be dissolved in the aqueous phase or employed in solid form, and a process of forming microcapsules and encapsulated compositions containing same, wherein the polyamine is employed in solid form represents a particular embodiment of the present invention. The applicant found the use of a solid polyamine to be particularly advantageous when the polyamine used as a shell-forming monomer is melamine. It was surprising that melamine in solid form could be used in this way. However, not only was it possible to carry out a poly-addition reaction at the oil-water interface with melamine in solid form, but in not having to dissolve the melamine, an undesirable and industrially impractical dilution step could be avoided. Without intending to be bound by any particular theory, it is believed that solid particles of poorly soluble polyamine, such as melamine, are absorbed or dissolved at the oil-water interface and in this way become available at the locus of the poly-addition reaction with other shell-forming monomers, and the reaction in turn appears to drive the process of further absorbing or dissolving the polyamine at the oil-water interface.

The polyamine in solid form may be employed in powder form, or it may be employed as a solid dispersion in an aqueous phase.

If not already incorporated into the oil-in-water emulsion, the shell-forming monomers may be added to the oil-in-water emulsion under stirring in accordance with the sequence of addition referred to hereinabove.

The shell-forming monomers in the oil-in-water emulsion are caused to react by adjusting the physical and/or chemical conditions within the emulsion. For example, the pH of the oil-in-water emulsion can be adjusted by increasing the pH. The pH may be raised above neutral; for example within an interval of about 7.5 to about 10, more particularly about 8 to about 9, and still more particularly 8.5±0.2. The pH adjustment step can be effected with additions of appropriate amounts of a suitable base, which may be in the form of a dilute solution (for example 20%) of ammonia, but other bases could be used. In order to avoid any undesired premature reaction of the shell-forming monomers, it is particularly preferred if the adjustment to increase the pH takes place after addition of the shell-forming monomer containing the plurality of olefinic double bonds, which typically would be the poly-functional acrylate.

In addition to increasing the pH of the oil-in-water emulsion, the temperature of the emulsion is elevated to a reaction temperature of about 40° C. to about 100° C., more particularly of about 50 to 95° C., still more particularly of about 70 and 90° C., for example 80±5° C. Heating is maintained for a period of time sufficient to at least partially cause the shell-forming monomers to react at the oil-water interface to form shells of thermosetting resin around the dispersed oil droplets, and thereby form an encapsulated composition in the form of a slurry of core-shell microcapsules. The time interval maintained at this elevated temperature may range from about 1 to 10 hours, more particularly for 2 to 6 hours, still more particularly from 2.5 to 4 hours, for example 3 hours.

The time taken to reach the reaction temperature may vary within an interval of about 15 minutes to more than 2 hours. Preferably, the time taken is 1.5 hours±0.5 hours.

In accordance with the process described herein, microcapsules can be obtained that exhibit good retention of their core contents, but are also rather frangible. In this way, the microcapsules are sufficiently robust that they exhibit low levels of leakage during storage even in extractive media, but in application a significant proportion can break relatively easily to release their core contents. This is particularly advantageous in encapsulated perfumery applications in which the encapsulated perfume is used to treat fabric or keratinous surfaces, and more particularly encapsulated perfumery in laundry applications. Prior art melamine-formaldehyde microcapsules tend to be very robust and only break to release perfume under high shear forces normally associated with handling treated dry fabric. However, microcapsules of the present invention break relatively easily during both wet stages and dry stages of application and can provide an olfactive boost across all stages of a cleaning or treatment process and beyond.

Applicant believes, although does not intend to be bound by particular theory that by operating within the process parameters described herein, including the selection of reagents, and in particular the control of the rate and/or duration of heating in the manner described, it is possible to control the reaction of the shell-forming monomers and create relatively thin and homogenous resinous shells, which resist leakage but which can break in response to only light or moderate shear force.

After formation of the microcapsules, the encapsulated composition can be cooled to room temperature. Preferably the cooling time is at least one hour, more particularly at least 2 hours, for example 2.5 hours±0.5 hours. Slow cooling in this manner is believed that the resin is able to further arrange itself by annealing, which may also affect the homogeneity of the resin shells and therefore contribute to the properties of the microcapsules in application.

Before, during or after cooling, the encapsulated composition may be further processed. Further processing may include treatment of the composition with one or more anti-microbial preservatives, which preservatives are well known in the art. Further processing may also include the addition of a suspending aid to the suspending medium, such as a hydrocolloid suspending aid to assist in the stable physical dispersion of the microcapsules and prevent any creaming or coalescence or whatsoever. Any additional adjuvants that may be desired, or conventional in the art may also be added at this time.

The resultant encapsulated composition, presented in the form of a slurry of microcapsules in an aqueous suspending medium may be incorporated as such in a consumer product base. If desired, however, the slurry may be dehydrated to present the encapsulated composition in dry powder form. Dehydration of a microcapsule slurry is conventional, and may be carried out according techniques known in the art, such as spray-drying, evaporation or lyophilization.

Typically, as is conventional in the art, dried microcapsules will be dispersed or suspended in a suitable powder, such as powdered silica or the like, which can act as a bulking agent, flow aid, or the like. Such suitable powder may be added to the encapsulated composition before, during or after the drying step.

A particular process of forming an encapsulated composition of the present invention comprises the steps of:—

Forming an oil-in-water emulsion comprising a polymeric stabilizer, an oil containing at least one functional ingredient such as a perfume or cosmetic ingredient, and an aqueous phase at a pH of about 3.5 to about 7, for example 4.5 or 6; preferably at an elevated temperature, more particularly 35±5° C.;

Maintaining the emulsion under stirring and at the aforementioned temperature for a period up to about 2 hours or more, for example 2 hours±0.5 hours;

Under stirring, adding the shell-forming monomers comprising a polyamine, more particularly melamine 1,2-phenylenediamine, 1,3-phenylenediamine, or 1,4-phenylenediamine, or a mixture thereof, and a polyfunctional acrylate selected from the group consisting of ((2,4,6-trioxocyclohexane-1,3,5-triyl)tris(oxy))tris(ethane-2,1-diyl) triacrylate, Tris(2-acryloyloxyethyl) Isocyanurate, 1,3,5-triacryloylhexahydro-1,3,5-triazine, or mixtures thereof, wherein the polyfunctional acrylate is preferably added before the addition of the polyamine;

Adjusting the pH of the emulsion to a pH of about 7.5 to about 10, more particularly between 8 to 9, for example 8.5±0.2 by means of the addition of a base, wherein the pH adjustment is preferably carried out between the addition of the polyfunctional acrylate and the polyamine;

Heating the emulsion to a reaction temperature of about 40 to about 100° C., more particularly of about 50 to 95° C., still more particularly of about 70 and 90° C., for example 80±5° C., wherein the temperature is elevated to the reaction temperature over a period of about 15 minutes to about 2 hours and more, for example 1.5 hours±0.5 hour, wherein said heating step may be carried out before, during or after the pH adjustment step;

Maintaining the emulsion at the reaction temperature for a period sufficient to at least partially cause the shell-forming monomers to react at the oil-water interface to form cross-linked resin shells around the dispersed oil droplets, thereby forming a slurry of core-shell microcapsules, wherein the time interval may range from about 0.5 to 10 hours, more particularly for 2 to 6 hours, still more particularly from 2.5 to 4 hours, for example 3 hours;

Cooling the slurry to room temperature, for example over a period of about 15 minutes to about 2 hours and more, for example 2 hour±0.5 hour;

Optionally processing the slurry, before, during or after the cooling step, by adding a microbial preservative, a suspending aid to aid the stable dispersion of the microcapsules in the slurry, and any other adjuvants that may be desired, or conventional in the art; and Optionally dehydrating the slurry to provide the encapsulated composition in the form of a powder.

Concerning the step of forming the oil-in-water emulsion, in a particular embodiment, the polymeric stabilizer can be formed in-situ by adding an aminosilane described above to the oil phase, and adding a maleic anhydride copolymer to the aqueous phase, and allowing the two to react under the conditions of pH and temperature referred to above to form the polymeric stabilizer.

Alternatively, in another particular embodiment, the polymeric stabilizer is a mixture of a maleic anhydride copolymer and polyvinyl alcohol.

Alternatively, or additionally, during the formation of a thermosetting resin shell, if desired, a mono-functional acrylate monomer may be added to the reaction mixture. In this way, the mono-functional acrylate monomer becomes embedded in the shell as the shell is in the process of being formed. Although it is possible to add the mono-functional acrylate monomer at the same time as the addition of melamine, preferably it is added at some time after the addition of melamine. More particularly, it is added at some time after the addition of melamine, and before the shell is fully formed.

Microcapsules prepared according to a process of the present invention may be coated with a coating material.

In a particular embodiment of the present invention, a coating material can be covalently grafted to the microcapsule shell. The grafting step may be carried out by treating core-shell microcapsules with a coating material that contains functional groups that are reactive with functional groups present in the shells of the core-shell microcapsules, such as any residual unreacted acrylate functional groups of the poly-functional acrylate shell-forming monomers.

As stated hereinabove, the coating material may be a pre-formed polymer, which can be covalently grafted to a microcapsule shell. Alternatively, it may be a polymer that is formed in-situ by the polymerization of suitable monomers during the coating process.

Preferably, coating materials are formed from polymerizable monomers that, upon activation, can react with residual acrylate functional groups present in a microcapsule shell. Particular polymerizable monomers suitable for forming coating mateirials include, but are not limited, to acrylates or methacrylates, such as methyl methacrylate (MMA), dimethylaminoethyl methacrylate (DMAEMA), and butyl methacrylate (BMA), and quaternized compounds containing an olefin group, such as diallyldimethylammonium chloride (DADMAC).

Accordingly, in a particular embodiment of the present invention there is provided a method of forming microcapsules and an encapsulated composition containing same, said method comprising the steps of:

forming a microcapsule slurry in accordance with the process described hereinabove;

adding a polymerizable monomer to the slurry and causing the monomer to both polymerize and react with residual acrylate functional groups contained within the microcapsule shells to form coating material covalently bound to the shells of the core-shell microcapsules.

The formation of the coating material and its grafting to the core-shell microcapsules is carried out at an elevated temperature, e.g. about 50° C. to about 100° C., more particularly from about 55 to 95° C., still more particularly from about 60 to about 90° C., for example 80±5° C. The reaction may be carried out over a period of about 1 hour to about 10 hours, more particularly from about 2 hours to about 8 hours, still more particularly from about 3 hours to about 6 hours. The reaction can be initiated with a free-radical initiator such as 2,2'-Azobisisobutyronitrile (AIBN), potassium persulfate (KPS), benzoyle peroxide (BPO), or any other initiator suitable for such purpose.

Functional ingredients that may be encapsulated in accordance with the present invention include, perfume ingredients, cosmetic actives, pheromones, optical brighteners, catalysts, and the mixtures thereof. In a particular embodiment, the functional ingredient is selected from one or more perfume ingredients.

Perfume ingredients for use in encapsulated compositions of the present invention may be selected from natural products such as essential oils, absolutes, resinoids, resins, concretes, and synthetic perfume components such as hydrocarbons, alcohols, aldehydes, ketones, ethers, acids, acetals, ketals and nitriles, including saturated and unsaturated compounds, aliphatic, carbocyclic and heterocyclic compounds, or precursors of any of the above. Other examples of odorant compositions which may be used are described in H 1468 (United States Statutory Invention Registration).

Examples of preferred perfume ingredients are any of those s selected from ADOXAL (2,6,10-trimethylundec-9-enal); AGRUMEX (2-(tert-butyl)cyclohexyl acetate); ALDEHYDE C 10 DECYLIC (decanal); ALDEHYDE C 11 MOA (2-methyldecanal); ALDEHYDE C 11 UNDECYLENIC (undec-10-enal); ALDEHYDE C 110 UNDECYLIC (undecanal); ALDEHYDE C 12 LAURIC (dodecanal); ALDEHYDE C 12 MNA PURE (2-methylundecanal); ALDEHYDE ISO C 11 ((E)-undec-9-enal); ALDEHYDE MANDARINE 10%/TEC ((E)-dodec-2-enal); ALLYL AMYL GLYCOLATE (allyl 2-(isopentyloxy)acetate); ALLYL CYCLOHEXYL PROPIONATE (allyl 3-cyclohexylpropanoate); ALLYL OENANTHATE (allyl heptanoate); AMBER CORE (1-((2-(tert-butyl)cyclohexyl)oxy)butan-2-ol); AMBERMAX (1,3,4,5,6,7-hexahydro-.beta.,1, 1,5,5-pentamethyl-2H-2,4a-Methanonaphthalene-8-ethanol); AMYL SALICYLATE (pentyl 2-hydroxybenzoate); APHERMATE (1-(3,3-dimethylcyclohexyl)ethyl formate); BELAMBRE ((1R,2S,4R)-2'-isopropyl-1,7,7-trimethylspiro[bicyclo[2.2.1]heptane-2,4'-[1,3]dioxane]); BIGARYL (8-(sec-butyl)-5,6,7,8-tetrahydroquinoline); BOISAMBRENE FORTE ((ethoxymethoxy)cyclododecane); BOISIRIS ((1S,2R,5R)-2-ethoxy-2,6,6-trimethyl-9-methylenebicyclo[3.3.1]nonane); BORNYL ACETATE ((2S,4S)-1,7,7-trimethylbicyclo[2.2.1]heptan-2-yl acetate); BUTYL BUTYRO LACTATE (1-butoxy-1-oxopropan-2-yl butyrate); BUTYL CYCLOHEXYL ACETATE PARA (4-(tert-butyl)cyclohexyl acetate); CARYOPHYLLENE ((Z)-4,11,11-trimethyl-8-methylenebicyclo[7.2.0]undec-4-ene); CASHMERAN (1,1,2,3,3-pentamethyl-2,3,6,7-tetrahydro-1H-inden-4(5H)-one); CASSYRANE (5-tert-butyl-2-methyl-5-propyl-2H-furan); CITRAL ((E)-3,7-dimethylocta-2,6-dienal); CITRAL LEMAROME N ((E)-3,7-dimethylocta-2, 6-dienal); CITRATHAL R ((Z)-1,1-diethoxy-3,7-dimethylocta-2,6-diene); CITRONELLAL (3,7-dimethyloct-6-enal); CITRONELLOL (3,7-dimethyloct-6-en-1-ol); CITRONELLYL ACETATE (3,7-dimethyloct-6-en-1-yl acetate); CITRONELLYL FORMATE (3,7-dimethyloct-6-en-1-yl formate); CITRONELLYL NITRILE (3,7-dimethyloct-6-enenitrile); CITRONELLYL PROPIONATE (3,7-dimethyloct-6-en-1-yl propionate); CLONAL (dodecanenitrile); CORANOL (4-cyclohexyl-2-methylbutan-2-ol); COSMONE ((Z)-3-methylcyclotetradec-5-enone); CYCLAMEN ALDEHYDE (3-(4-isopropylphenyl)-2-methylpropanal); CYCLOGALBANATE (allyl 2-(cyclohexyloxy)acetate); CYCLOHEXYL SALICYLATE (cyclohexyl 2-hydroxybenzoate); CYCLOMYRAL (8,8-dimethyl-1,2,3,4,5,6,7,8-octahydronaphthalene-2-carbaldehyde); DAMASCENONE ((E)-1-(2,6,6-trimethylcyclohexa-1,3-dien-1-yl)but-2-en-1-one); DAMASCONE ALPHA ((E)-1-(2,6,6-trimethylcyclohex-2-en-1-yl)but-2-en-1-one); DAMASCONE DELTA ((E)-1-(2,6,6-trimethylcyclohex-3-en-1-yl)but-2-en-1-one); DECENAL-4-TRANS ((E)-dec-4-enal); DELPHONE (2-pentylcyclopentanone); DIHYDRO ANETHOLE (propanedioic acid 1-(1-(3,3-dimethylcyclohexyl)ethyl) 3-ethyl ester); DIHYDRO JASMONE (3-methyl-2-pentylcyclopent-2-enone); DIMETHYL BENZYL CARBINOL (2-methyl-1-phenylpropan-2-ol); DIMETHYL BENZYL CARBINYL ACETATE (2-methyl-1-phenylpropan-2-yl acetate); DIMETHYL BENZYL CARBINYL BUTYRATE (2-methyl-1-phenylpropan-2-yl butyrate); DIMETHYL OCTENONE (4,7-dimethyloct-6-en-3-one); DIMETOL (2,6-dimethylheptan-2-ol); DIPENTENE (1-methyl-4-(prop-1-en-2-yl)cyclohex-1-ene); DUPICAL ((E)-4-((3aS,7aS)-hexahydro-1H-4,7-methanoinden-5(6H)-ylidene)butanal); EBANOL ((E)-3-methyl-5-(2,2,3-trimethylcyclopent-3-en-1-yl)pent-4-en-2-ol); ETHYL CAPROATE (ethyl hexanoate); ETHYL CAPRYLATE (ethyl octanoate); ETHYL LINALOOL ((E)-3,7-dimethylnona-1,6-dien-3-01); ETHYL LINALYL ACETATE ((Z)-3,7-dimethylnona-1,6-dien-3-yl acetate); ETHYL OENANTHATE (ethyl heptanoate); ETHYL SAFRANATE (ethyl 2,6,6-trimethylcyclohexa-1,3-diene-1-carboxylate); EUCALYPTOL ((1s,4s)-1,3,3-trimethyl-2-oxabicyclo[2.2.2]octane); FENCHYL ACETATE ((2S)-1,3,3-trimethylbicyclo[2.2.1]heptan-2-yl acetate); FENCHYL ALCOHOL ((1S,2R,4R)-1,3,3-trimethylbicyclo[2.2.1]heptan-2-ol); FIXOLIDE (1-(3,5,5,6,8,8-hexamethyl-5,6,7,8-tetrahydronaphthalen-2-yl)ethanone); FLORALOZONE (3-(4-ethylphenyl)-2,2-dimethylpropanal); FLORHYDRAL (3-(3-isopropylphenyl)butanal); FLOROCYCLENE ((3aR, 6S,7aS)-3a,4,5,6,7,7a-hexahydro-1H-4,7-methanoinden-6-yl propionate); FLOROPAL (2,4,6-trimethyl-4-phenyl-1,3-dioxane); FRESKOMENTHE (2-(sec-butyl)cyclohexanone); FRUITATE ((3aS,4S,7R,7aS)-ethyl octahydro-1H-4,7-methanoindene-3a-carboxylate); FRUTONILE (2-methyldecanenitrile); GALBANONE PURE (1-(3,3-dimethylcyclohex-1-en-1-yl)pent-4-en-1-one); GARDOCYCLENE ((3aR,6S,7aS)-3a,4,5,6,7,7a-hexahydro-1H-4,7-methanoinden-6-yl isobutyrate); GERANIOL ((E)-3,7-dimethylocta-2,6-dien-1-ol); GERANYL ACETATE SYNTHETIC ((E)-3,7-dimethylocta-2,6-dien-1-yl acetate); GERANYL ISOBUTYRATE ((E)-3,7-dimethylocta-2,6-dien-1-yl isobutyrate); GIVESCONE (ethyl 2-ethyl-6,6-dimethylcyclohex-2-enecarboxylate); HABANOLIDE ((E)-oxacyclohexadec-12-en-2-one); HEDIONE (methyl 3-oxo-2-pentylcyclopentaneacetate); HERBANATE ((2S)-ethyl 3-isopropylbicyclo[2.2.1]hept-5-ene-2-carboxylate); HEXENYL-3-CIS BUTYRATE ((Z)-hex-3-en-1-yl butyrate); HEXYL CINNAMIC ALDEHYDE ((E)-2-benzylideneoctanal); HEXYL ISOBUTYRATE (hexyl isobutyrate); HEXYL SALICYLATE (hexyl 2-hydroxybenzoate); INDOFLOR (4,4a,5,9b-tetrahydroindeno[1,2-d][1,3]dioxine); IONONE BETA ((E)-4-(2,6,6-trimethylcyclohex-1-en-1-yl)but-3-en-2-one); IRISONE ALPHA ((E)-4-(2,6,6-trimethylcyclohex-2-en-1-yl)but-3-en-2-one); IRONE ALPHA ((E)-4-(2,5,6,6-tetramethylcyclohex-2-en-1-yl)but-3-en-2-one); ISO E SUPER (1-(2,3,8,8-tetramethyl-1,2,3,4,5,6,7,8-octahydronaphthalen-2-yl)ethanone); ISOCYCLOCITRAL (2,4,6-trimethylcyclohex-3-enecarbaldehyde); ISO NONYL ACETATE (3,5,5-trimethyl hexyl acetate); ISOPROPYL METHYL-2-BUTYRATE (isopropyl 2-methyl butanoate); ISORALDEINE 70 ((E)-3-methyl-4-(2,6,6-trimethylcyclohex-2-en-1-yl)but-3-en-2-one); JASMACYCLENE ((3aR,6S,7aS)-3a,4,5,6,7,7a-hexahydro-1H-4,7-methanoinden-6-yl acetate); JASMONE CIS ((Z)-3-methyl-2-(pent-2-en-1-yl)cyclopent-2-enone); KARANAL (5-(sec-butyl)-2-(2,4-dimethylcyclohex-3-en-1-yl)-5-methyl-1,3-dioxane); KOAVONE ((Z)-3,4,5,6,6-pentamethylhept-3-en-2-one); LEAF ACETAL ((Z)-1-(1-ethoxyethoxy)hex-3-ene); LEMONILE ((2E,6Z)-3,7-dimethylnona-2,6-dienenitrile); LIFFAROME GIV ((Z)-hex-3-en-1-yl methyl carbonate); LILIAL (3-(4-(tert-butyl)phenyl)-2-methylpropanal); LINALOOL (3,7-dimethylocta-1,6-dien-3-ol); LINALYL ACETATE (3,7-dimethylocta-1,6-dien-3-yl acetate); MAHONIAL ((4E)-9-hydroxy-5,9-dimethyl-4-decenal); MALTYL ISOBUTYRATE (2-methyl-4-oxo-4H-pyran-3-yl isobutyrate); MANZANATE (ethyl 2-methylpentanoate); MELONAL (2,6-dimethylhept-5-enal); MENTHOL (2-isopropyl-5-methylcyclohexanol); MENTHONE (2-isopropyl-5-methylcyclohexanone); METHYL CEDRYL KETONE (1-((1S,8aS)-1,4,4,6-tetramethyl-2,3,3a,4,5,8-hexahydro-1H-5,8a-methanoazulen-7-yl)ethanone); METHYL NONYL KETONE EXTRA (undecan-2-one); METHYL OCTYNE CARBONATE (methyl non-2-ynoate); METHYL PAMPLEMOUSSE (6,6-dimethoxy-2,5,5-trimethylhex-2-ene); MYRALDENE (4-(4-methylpent-3-en-1-yl)cyclohex-3-enecarbaldehyde); NECTARYL (2-(2-(4-methylcyclohex-3-en-1-yl)propyl)cyclopentanone); NEOBERGAMATE FORTE (2-methyl-6-methyleneoct-7-en-2-yl acetate); NEOFOLIONE ((E)-methyl non-2-enoate); NEROLIDYLE ((Z)-3,7,11-trimethyldodeca-1,6,10-trien-3-yl acetate); NERYL ACETATE HC ((Z)-3,7-dimethylocta-2,6-dien-1-yl acetate); NONADYL (6,8-dimethylnonan-2-ol); NONENAL-6-CIS ((Z)-non-6-enal); NYMPHEAL (3-(4-isobutyl-2-methylphenyl)propanal); ORIVONE (4-(tert-pentyl)cyclohexanone); PARADISAMIDE (2-ethyl-N-methyl-N-(m-tolyl)butanamide); PELARGENE (2-methyl-4-methylene-6-phenyltetrahydro-2H-pyran); PEONILE (2-cyclohexylidene-2-phenylacetonitrile); PETALIA (2-cyclohexylidene-2-(o-tolyl)acetonitrile); PIVAROSE (2,2-dimethyl-2-pheylethyl propanoate); PRECYCLEMONE B (1-methyl-4-(4-methylpent-3-en-1-yl)cyclohex-3-enecarbaldehyde); PYRALONE (6-(sec-butyl)quinoline); RADJANOL SUPER ((E)-2-ethyl-4-(2,2,3-trimethylcyclopent-3-en-1-yl)but-2-en-1-ol); RASPBERRY KETONE (N112) (4-(4-hydroxyphenyl)butan-2-one); RH UBAFURANE (2,2,5-trimethyl-5-pentylcyclopentanone); ROSACETOL (2,2,2-trichloro-1-phenylethyl acetate); ROSALVA (dec-9-en-1-ol); ROSYFOLIA ((1-methyl-2-(5-methylhex-4-en-2-yl)cyclopropyl)-methanol); ROSYRANE SUPER (4-methylene-2-phenyltetrahydro-2H-pyran); SERENOLIDE (2-(1-(3,3-dimethylcyclohexyl)ethoxy)-2-methylpropyl cyclopropanecarboxylate); SILVIAL (3-(4-isobutylphenyl)-2-methylpropanal); SPIROGALBANONE (1-(spiro[4.5]dec-6-en-7-yl)pent-4-en-1-one); STEMONE ((E)-5-methylheptan-3-one oxime); SUPER MUGUET ((E)-6-ethyl-3-methyloct-6-en-1-ol); SYLKOLIDE ((E)-2-((3,5-dimethylhex-3-en-2-yl)oxy)-2-methylpropyl cyclopropanecarboxylate); TERPINENE GAMMA (1-methyl-4-propan-2-ylcyclohexa-1,4-diene); TERPINOLENE (1-methyl-4-(propan-2-ylidene)cyclohex-1-ene); TERPINYL ACETATE (2-(4-methylcyclohex-3-en-1-yl)propan-2-yl acetate); TETRAHYDRO LINALOOL (3,7-dimethyloctan-3-ol); TETRAHYDRO MYRCENOL (2,6-dimethyloctan-2-ol); THIBETOLIDE (oxacyclohexadecan-2-one); TRIDECEN E-2-NITRILE ((E)-tridec-2-enenitrile); UNDECAVERTOL ((E)-4-methyldec-3-en-5-ol); VELOUTONE (2,2,5-trimethyl-5-pentylcyclopentanone); VIRIDINE ((2,2-dimethoxyethyl)benzene); ZINARINE (2-(2,4-dimethylcyclohexyl)pyridine); and mixture thereof.

In another particular embodiment, the functional ingredient is a cosmetic active. Preferably, the cosmetic actives have a calculated octanol/water partition coefficient (ClogP) of 1.5 or more, more preferably 3 or more. Preferably, the ClogP of the cosmetic active is from about 2 to about 7.

Particularly useful cosmetic actives may be selected from the group consisting of emollients, smoothening actives, hydrating actives, soothing and relaxing actives, decorative actives, deodorants, anti-aging actives, draining actives, remodelling actives, skin levelling actives, preservatives, anti-oxidants, antibacterial or bacteriostatic actives, cleansing actives, lubricating actives, structuring actives, hair conditioning actives, whitening actives, texturing actives, softening actives, anti-dandruff actives, and exfoliating actives.

Particularly useful cosmetic actives include, but are not limited to hydrophobic polymers, such as alkyldimethylsiloxanes, polymethylsilsesquioxanes, polyethylene, polyisobutylene, styrene-ethylene-styrene and styrene-butylene-styrene block copolymers, and the like; mineral oils, such as hydrogenated isoparaffins, silicone oils and the like; vegetable oils, such as argan oil, jojoba oil, aloe vera oil, and the like; fatty acids and fatty alcohols and their esters; glycolipides; phospholipides; sphingolipides, such as ceramides; sterols and steroids; terpenes, sesquiterpenes, triterpenes and their derivatives; essential oils, such as *Arnica* oil, *Artemisia* oil, Bark tree oil, Birch leaf oil, Calendula oil, Cinnamon oil, *Echinacea* oil, *Eucalyptus* oil, *Ginseng* oil, Jujube oil, *Helianthus* oil, Jasmine oil, Lavender oil, Lotus seed oil, *Perilla* oil, Rosmary oil, Sandal wood oil, Tea tree oil, Thyme oil, Valerian oil, Wormwood oil, Ylang Ylang oil, *Yucca* oil and the like.

In an embodiment, the cosmetic active may be selected from the group consisting of Sandal wood oil, such as Fusanus Spicatus kernel oil; Panthenyl triacetate (CAS-No: 94089-18-6); Tocopheryl acetate (CAS-No: 7695-91-2); Tocopherol (CAS-No: 1406-66-2/10191-41-0/2074-53-5/59-02-9/148-03-8/119-13-1/54-28-4); Naringinin (CAS-No: 480-41-1); Ethyl linoleate; Farnesyl acetate; Farnesol; Citronellyl methyl crotonate (CAS-No: 20770-40-5); Ceramide-2 (1-Stearoiyl-C18-Sphingosine, CAS-No: 100403-19-8); and mixtures thereof.

Encapsulated compositions of the present invention may be employed as a delivery system to deliver active ingredients, such as perfumes for use in all manner of consumer products. The term "consumer products" refers in particular to home-care, textile-care or personal-care products, such as body-care and hair-care products.

Encapsulated compositions according to the invention are particularly usefully employed as perfume delivery vehicles in consumer products that require, in order to deliver optimal perfumery benefits, that the microcapsules adhere well to the substrate on which they are applied. Such consumer products include hair shampoos and conditioners, as well as textile-treatment products, such as laundry detergents and conditioners.

There now follows a series of examples that serve to further illustrate the invention.

Example 1

Preparation of 1,3-phenylenediamine-1,3,5-triacryloylhexahydro-1,3,5-triazine microcapsules In this example, formaldehyde-free 1,3-phenylenediamine-1,3,5-triacryloylhexahydro-1,3,5-triazine (TAHHT) microcapsules were prepared by performing the steps of:
1) Preparing the core composition comprising 3-aminopropyltriethoxy silane by admixing 0.5 g 3-aminopropyltriethoxy silane and 35 g fragrance composition;

2) Emulsifying the core composition obtained in step 1) in a mixture of 39 g water and 15 g aqueous solution of hydrolyzed Zemac e400 at 10 wt % (=1.5 g solid Zemac e400), by using a cross-beam stirrer with pitched bean operating at a stirring speed of 600 rpm at a temperature of 35±2° C.;
3) Adjusting the pH to 6.0±0.2 with 1.3 g of a 20% $NH_3$ solution in water and maintaining the system at a temperature of 35±2° C. for 1 hour while maintaining stirring as in step 2);
4) Adding 1.2 g of 1,3-phenylenediamine (PDA) and then adding 2.2 g 1,3,5-triacryloylhexahydro-1,3,5-triazine (TAHHT), increasing the pH to 8.7±0.2 by addition of 1.7±1 g of 20% $NH_3$ solution in water, while maintaining stirring as in step 2);
5) Heating the mixture obtained in step 3 to 80±5° C. in 120±5 minutes and maintaining this temperature and stirring for 30 minutes in order to obtain a slurry of microcapsules.
6) Adding 0.2 g of 0.2 M AIBN solution in toluene and 3.0 g of 4% aqueous solution of KPS, followed by 1.0 g of methyl methacrylate, and maintaining the stirring and the temperature at 80° C. for 60 minutes;
7) Cooling down the slurry to room temperature during a period of 120 minutes.

The solid content of the slurry was measured by using a thermo-balance operating at 120° C. The solid content, expressed as weight percentage of the initial slurry deposited on the balance was taken at the point where the drying-induced rate of weight change had dropped below 0.1 wt %/min. The solid content was 40.9 wt %, based on the total weight of the slurry (microcapsules+aqueous phase). The yield of encapsulation, expressed as the ratio of the encapsulated fragrance composition divided by nominal amount of fragrance composition was 99%. The volume average diameter of the capsules was Dv(50)=15.8 μm. The amine to olefinic double bond ratio was 0.83.

Example 2

Preparation of Formaldehyde-Free Melamine-Acrylate Microcapsules with Polymaleic Anhydride Copolymer and Polyvinyl Alcohol as Emulsifier System In this example), formaldehyde-free melamine—pentaerythritol tetraacrylate microcapsules were prepared by performing the steps of:
1) Emulsifying 36.8 g of perfume in an aqueous phase comprising 41 g water and 5.2 g aqueous solution of hydrolyzed Zemac e400 at 10 wt % (=0.52 g solid Zemac e400, obtained by dissolving the polymer as received in water at 90° C. for 1 hour) and 10.5 g of Kuraray Poval 23/88 at 10% solution (=1.05 g solid Poval 23/88) in water, the pH of which has been adjusted to 4.4±0.2 with 0.7 g of a 20% NH3 solution in water, by using a cross-beam stirrer with pitched bean operating at a stirring speed of 600 rpm at a temperature of 36±2° C. for 1.5 hour.
2) Adding 1.1 g of melamine in powder form and then 2.9 g of pentaerythritol tetraacrylate (PETA), increasing the pH to 8.7±0.2 by addition of 3.8±1 g of 20% NH3 solution in water, while maintaining stirring as in step 1);
3) Heating the mixture obtained in step 2 to 80±5° C. in 1 hours and maintaining this temperature and stirring for 3 hours in order to obtain a slurry of microcapsules.
4) Adding 3 g of a 4% potassium peroxodisulfate (KPS) solution in water and 0.2 g azoisobutyronitrile (AIBN) to the slurry obtained in step 3), followed by 1 g of methyl methacrylate in order to let methyl methacrylate polymerize by free radical polymerization during one additional hour at 80±5° C., and under continuous stirring.
5) Cooling down the slurry to room temperature over a period of 2 hours.

The solid content of the slurry was measured by using a thermo-balance operating at 120° C. The solid content, expressed as weight percentage of the initial slurry deposited on the balance was taken at the point where the drying-induced rate of weight change had dropped below 0.1%/min. The solid content of EXAMPLE 1 was 42.6 wt %, referred to the slurry. The yield of encapsulation, expressed as the ratio of the encapsulated fragrance composition divided by nominal amount of fragrance composition was 100%. The volume average diameter of the capsules was Dv(50)=17.7 μm. The amine to olefinic double bond ratio was 0.82.

Example 3

In this comparative example, conventional aminoplast microcapsules were prepared according to the method disclosed in WO 2017001672 A1, Example 1.

Example 4

In this comparative example, conventional polyurethane microcapsules were prepared according to the method disclosed in WO 2016071152 A1, Example 2.

Example 5

Assessment of Leakage of a Microcapsule Slurry in a Model Extractive Medium

The model extractive medium is a system consisting of an aqueous solution of ethanol at an initial concentration of 5 vol % co-existing with an immiscible cyclohexane phase.

In a first step, 10 ml of cyclohexane are put into a vial. Second, 1.8 ml of a 5 vol % ethanol in water is added to the vial. After equilibration, taking into account the partition coefficient of ethanol between cyclohexane and the water of 0.03 (see A. W. Islam, A. Zavvadi, V. N. Kabadi, Chem. Process Eng., 2012, 33 (2), 243-253), the percentage of ethanol in the aqueous phase is 4.2±0.5 vol % and the percentage of ethanol referred to the whole system is 0.4±0.05 vol %.

In a second step, the slurry to be assessed is diluted in such a way that the perfume concentration in the diluted slurry is about 10 wt % and 200 microliters of this diluted slurry are added to the vial.

In a third step, the vial is submitted to a horizontal mixing on an elliptic xy-mixing equipment operating at a 250 rpm for 4 hours (shaking in the z direction is avoided).

In a fourth step, the upper cyclohexane phase containing the extracted perfume is analysed spectrophotometrically by using a UV/visible light spectrometer. The perfume concentration is determined by measuring the intensity of the absorbed UV/visible light at the maximum absorbance wavelength, which has been determined previously by using a reference perfume/cyclohexane solution of known concentration. This latter reference solution is used as an external standard for the quantification of the extracted perfume. The leakage value is defined as the percentage of the encapsulated perfume that has been recovered in the hexane phase.

Representative leakage values are given in Table 1, hereunder.

Example 6

Assessment of Fragrance Release Performance

The release performance of the microcapsule slurries was measured by using a texture analyzer (TA XT PLUS, ex TA instruments). 300 microliters of undiluted slurry were deposited on the surface of filter paper in three successive applications of 100 microliters and left to dry overnight). Then, the lower surface of a mechanical sensor probe, consisting of a flat metal cylinder having a diameter of 12.5 mm, is applied on the deposited microcapsules with a force of 100 N and a penetration velocity of 0.01 mm/s.

As the probe penetrates the bed of microcapsules deposited on the filter paper, it experiences a back elastic force which is proportional to the elastic bending modulus of the microcapsules, which is inversely proportional to the release performance of the microcapsules. The value of the measured force at the 50% deformation of the microcapsule bed is taken as a measurement of the release performance of the microcapsules. The displacement corresponding to 50% deformation point is determined as the half way point between the displacement point where the first contact with the microcapsules occurs, which is marked by the onset of a back force and the point where the probe motion is stopped by the filter paper.

TABLE 1

Perfume leakage in water/ethanol/cyclohexane and force at 50% deformation for selected EXAMPLES 1.1 to 3.1.

| Example | Leakage at 5 vol % EtOH [wt %] | Force at 50% deformation [N] |
| --- | --- | --- |
| EXAMPLE 2 (PDA/TAHHT/ZeMac/aminosilane) | 3 | 2.0 |
| | 3 | 3.0 |
| EXAMPLE 3 (comparative aminoplast example) | 2 | 9.0 |
| | 1 | 11.0 |
| EXAMPLE 3 (comparative polyurea example) | 11 | 24.0 |
| | 18 | 26.0 |
| | 16 | 23.0 |

As apparent from Table 1 microcapsules based on new polyamine-polyfunctional acrylate provides microcapsules that exhibit similar or even better stability and/or release performance than the comparative formaldehyde-based aminoplast microcapsules according to the prior art.

We claim:

1. A core-shell microcapsule comprising a core containing a perfume ingredient and a shell surrounding or at least partially surrounding said core, the shell comprising a thermosetting resin formed by the reaction of shell-forming monomers comprising a polyamine and a material comprising a plurality of olefinic double bonds, wherein the olefinic double bonds are in conjugation with an electron-withdrawing group, wherein the material comprising the plurality of olefinic double bonds is capable of reacting with the polyamine, wherein the amino groups of the shell-forming monomers comprising a polyamine react with double bonds of the material comprising a plurality of olefinic double bonds to form the thermosetting resin, and wherein the polyamine is not a polyamine-alkylol precondensate.

2. An encapsulated composition comprising a plurality of microcapsules according to claim 1 suspended in a suspending medium.

3. An encapsulated composition according to claim 2, wherein the thermosetting resin is formed by the reaction of a polyamine and a polyfunctional acrylate.

4. An encapsulated composition according to claim 3, wherein the poly-functional acrylate is selected from the group consisting of pentaerythritol-tetraacrylate (PETA), pentaerythritol triacrylate (PETIA), 1,4-butanediol diacrylate (BDA-2), ethylene glycol dimethacrylate (EDGMA), trimethylolpropane triacrylate (TMPTA), hexane diol diacrylate(HDDA), ((2,4,6-trioxocyclohexane-1,3,5-triyl)tris(oxy))tris(ethane-2, 1-diyl)triacrylate (TOCTA), tris(2-acryloyloxyethyl) isocyanurate, 1,3,5 -triacryloylhexahydro-1,3,5-triazine (TAHHT) and mixtures thereof.

5. An encapsulated composition according to claim 2, wherein the polyamine is selected from the group consisting of ethylene diamine, bis(2-aminoethyl)amine, melamine, 3,5-diamino-1,2,4-triazole, 2,4-diamino-6-phenyl-1,3,5-triazine, 6-methyl-1,3,5-triazine-2,4-diamine, 1,2-phenylendiamine, 1,3-phenylenediamine or 1,4-phenylenediamine and mixtures thereof.

6. An encapsulated composition according to claim 2, wherein the core-shell microcapsule is at least partially coated with a coating material.

7. An encapsulated composition according to claim 6, wherein the coating material is covalently bound to the shell of the core-shell microcapsule.

8. An encapsulated composition according to claim 6, wherein the coating material is polymethyl methacrylate.

9. A method of preparing an encapsulated composition according to claim 2, comprising the steps of:
   a. forming an oil-in-water emulsion, wherein the oil phase comprises a perfume ingredient-containing at least one oil droplet dispersed in an aqueous external phase;
   b. causing shell-forming monomers present in the oil-in-water emulsion to react at the oil-water interface, to form an encapsulating thermosetting resin shell around the oil droplet, thereby forming the microcapsule.

10. A method according to claim 9, wherein the polyamine shell-forming monomer is added to the emulsion in solid form.

11. A method according to claim 9, further comprising the step of:
   c. at least partially coating the thermoset resin shell with a coating material.

12. A consumer product selected from a laundry care product, a personal care product or a household care product, comprising an encapsulated perfume composition according to claim 2.

* * * * *